(12) United States Patent
Nagata

(10) Patent No.: US 7,799,911 B2
(45) Date of Patent: Sep. 21, 2010

(54) PHTHALOCYANINE COMPOUND AND METHOD FOR PRODUCING THE SAME, AND COLORING COMPOSITION CONTAINING THE PHTHALOCYANINE COMPOUND

(75) Inventor: Yoshiaki Nagata, Sakurai (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 276 days.

(21) Appl. No.: 11/816,484

(22) PCT Filed: Feb. 17, 2006

(86) PCT No.: PCT/JP2006/302842

§ 371 (c)(1),
(2), (4) Date: Aug. 16, 2007

(87) PCT Pub. No.: WO2006/088140

PCT Pub. Date: Aug. 24, 2006

(65) Prior Publication Data

US 2009/0018328 A1    Jan. 15, 2009

(30) Foreign Application Priority Data

Feb. 18, 2005  (JP) ............................. 2005-042135
Jun. 9, 2005   (JP) ............................. 2005-169353

(51) Int. Cl.
C07B 47/00  (2006.01)
C07D 487/22  (2006.01)

(52) U.S. Cl. ..................................... 540/145
(58) Field of Classification Search ................. 540/145
See application file for complete search history.

(56) References Cited

FOREIGN PATENT DOCUMENTS

EP           0266219 A2    5/1988
JP           200164534 A   3/2001

OTHER PUBLICATIONS

E.V. Kudrik et al.; Synthesis and properties of 5, 6-dicyanobenzimidazole and porphyrazines derived from it, Russian Journal of General Chemistry, 1999, vol. 69, No. 8, pp. 1321-1324. Chemical Abstracts, 2000, vol. 132, abstract No. 334445.
C. Pardo et al.; "Tetraimidazophthalocyanines", Journal of Porphyrins and Phthalocyanines, 2000, vol. 4, No. 5, pp. 505-509. Chemical Abstracts, 2000, vol. 133, abstract No. 239362.
E. V. Kudrik et al.; "Synthesis and properties of 5, 6-dicyanobenzimidazole and porphyrazines derived from it", Russian Journal of General Chemistry, vol. 69, No. 8, pp. 1321-1324, Chemical Abstracts, 2000, vol. 132, abstract No. 334445. Cited in the ISR.
C. Pardo et al.; "Tetraimidazophthalocyanines" Journal of Porphyrins and Phthalocyanines, 2000, vol. 4, No. 5, pp. 505-509. Chemical Abstracts, 2000, vol. 133, abstract No. 239362. Cited in the ISR.

International Search Report of PCT/JP2006/302842, date of mailing Apr. 4, 2006.
Eva H. Mørkved et al., "Preparations and Template Cyclotetramerisations of 2,1,3-Benzothia(selena)diazole-5,6-dicarbonitriles", Acta Chemica Scandinavica, Nov. 1, 1994, pp. 658-662, vol. 49, XP-002580517.
A.E. Balakirev et al., "Synthesis and Properties of Copper(II) Tetra(2-alkyl-4,5-benzimidazolo)- and Tetra(2,2'-Dimethyl-4,5-benzodiazepino)porphyrazines", Russian Journal of General Chemistry, Dec. 29, 2000, vol. 72, No. 10, 2002, pp. 1616-1619, translated from Zhurnal Obshchei Khimii, XP-009080596.
Evgeny V. Kudrik et al., "Symmetrical tetrasubstituted phtHalocyanines containing condensed 2-alkylimidazole units", Mendeleev Commun., Nov. 3, 1998, vol. 9(2), pp. 85-86.
European Search Report dated May 26, 2010, issued in European Patent Application No. 06713983.

*Primary Examiner* — James O. Wilson
*Assistant Examiner* — Paul V. Ward
(74) *Attorney, Agent, or Firm* — Westerman, Hattori, Daniels & Adrian, LLP

(57) ABSTRACT

To provide a phthalocyanine compound represented by the following general formula (1), which is halogen-free and has green hue, and also has resistance to an organic solvent and an acid:

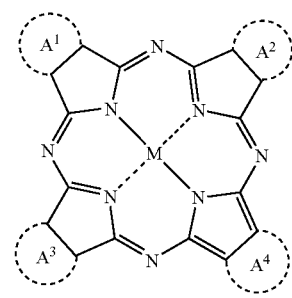

(1)

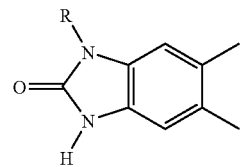

(2)

in the above general formula (1), M represents a divalent to tetravalent metal atom or two hydrogen atoms, and rings $A^1$, $A^2$, $A^3$ and $A^4$ each independently represents a benzene ring or a structure represented by the above general formula (2), provided that at least one of rings $A^1$, $A^2$, $A^3$ and $A^4$ is a structure represented by the general formula (2) and, in the above general formula (2), R represents a hydrogen atom, an alkyl group having 1 to 4 carbon atoms, a phenyl group, a tolyl group, or a xylyl group.

11 Claims, 5 Drawing Sheets

PHTHALOCYANINE COMPOUND AND METHOD FOR PRODUCING THE SAME, AND COLORING COMPOSITION CONTAINING THE PHTHALOCYANINE COMPOUND

TECHNICAL FIELD

The present invention relates to a phthalocyanine compound which can be used as a green pigment, and a method for producing the same, and a coloring composition containing the phthalocyanine compound.

BACKGROUND ART

Typical examples of a conventionally known green pigment include a polyhalogenated copper phthalocyanine. Since this polyhalogenated copper phthalocyanine has excellent fastness properties but has a large amount of halogen atoms such as chlorine and bromine atoms in the molecule, there have some fear for the safety and environmental burden, recently. Therefore, it is required to develop a pigment capable of coloring green with a compound having no halogen atom.

As a method of coloring green with a compound having no halogen atom (hereinafter referred to as "halogen-free"), for example, there is proposed a method comprising mixing copper phthalocyanine as a blue pigment with a yellow organic pigment, thereby performing toning to obtain a green pigment, and using the resulting green pigment (see, for example, Japanese Unexamined Patent Publication (Kokai) No. 2001-64534). However, this method causes a problem that segregation occurs because two kinds of pigments, each having a quite different chemical structure, are mixed, and also causes a problem that hue remarkably varies when exposed to sunlight because light resistance varies depending on the kind of the pigment mixed.

On the other hand, as a halogen-free compound which has green hue itself for example, a phthalocyanine compound having an imidazole ring represented by the following general formula (a) (hereinafter referred to as a "compound (a)") (see, for example, Russian Journal of General Chemistry, 69 (8), 1321 (1999) and Journal of Porphyrins and Phthalocyanines, 4, 505 (2000)). However, the above problem such as segregation is solved by the compound (a) in this method, but there was a problem that resistance to an organic solvent or an acid is insufficient

[Chemical Formula 1]

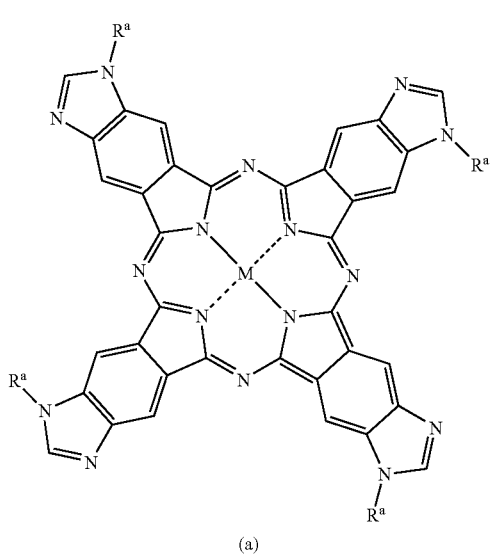

(a)

wherein M represents a copper atom or two hydrogen atoms, and $R^a$ represents any one of a hydrogen atom, a methyl group, and a benzyl group.

DISCLOSURE OF THE INVENTION

An object of the present invention is to provide a phthalocyanine compound which is halogen-free and has green hue, and also has resistance to an organic solvent and an acid.

The present inventors have intensively studied so as to achieve the above object and found that a compound prepared by introducing imidazolone into phthalocyanine is halogen-free and has green hue, and also has resistance to an organic solvent and an acid.

Namely, the present invention provides a phthalocyanine compound represented by the following general formula (1):

[Chemical Formula 2]

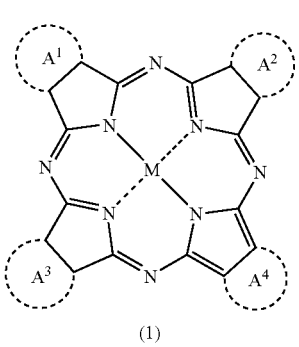

(1)

wherein M represents a divalent to tetravalent metal atom or two hydrogen atoms, and rings $A^1$, $A^2$, $A^3$ and $A^4$ each independently represents a benzene ring or a structure represented by the following general formula (2), provided that at least one of rings $A^1$, $A^2$, $A^3$ and $A^4$ is a structure represented by the following general formula (2):

[Chemical Formula 3]

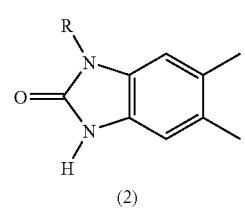

(2)

wherein R represents a hydrogen atom, an alkyl group having 1 to 4 carbon atoms, a phenyl group, a tolyl group, or a xylyl group.

The phthalocyanine compound of the present invention has green hue and also has resistance to an organic solvent and an acid, and is therefore useful as a green pigment. Also, the phthalocyanine compound of the present invention is halogen-free and therefore has features such as high safety and low environmental burden. Accordingly, the phthalocyanine compound of the present invention is used very usefully in place of a halogenated phthalocyanine-based pigment as an existing green pigment in applications which require environmental measures.

The phthalocyanine compound of the present invention can be used as a coloring agent in wide applications such as printing inks, coating materials, colored plastics, toners, ink jet inks, and color filters because of having the features described above.

BEST MODE FOR CARRYING OUT THE INVENTION

Figure 1:
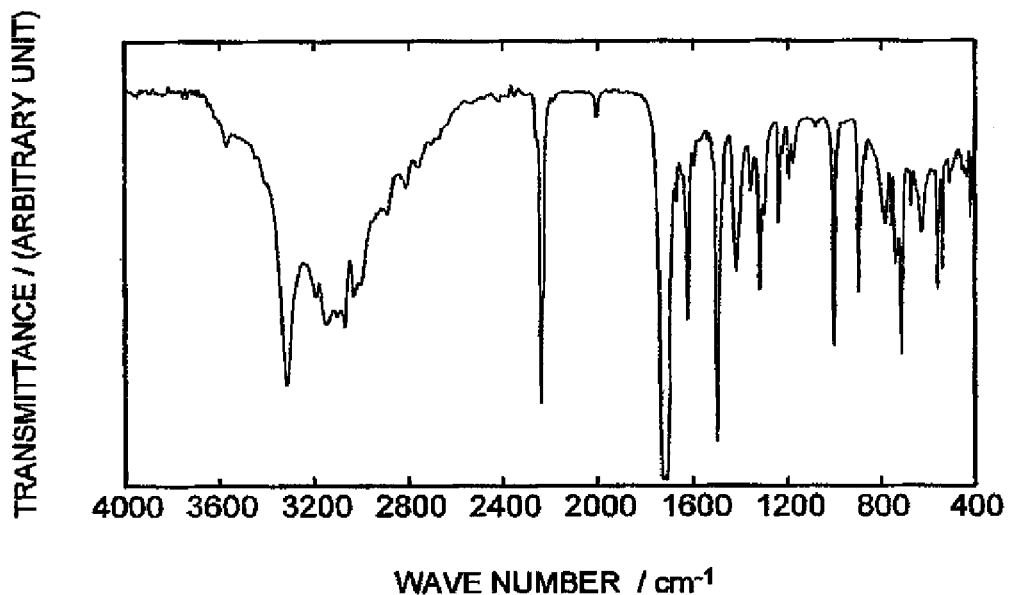
FIG. 1 is a graph showing an infrared spectrum of 5,6-dicyano benzimidazolone synthesized in Synthesis Example 1.

Synthesis Examples of a phthalocyanine compound represented by the following general formula (1) (hereinafter referred to as a "compound (1)") of the present invention are described below:

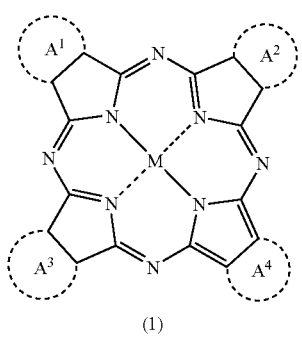

[Chemical Formula 4]

(1)

wherein M represents a divalent to tetravalent metal atom or two hydrogen atoms, and rings $A^1$, $A^2$, $A^3$ and $A^4$ each independently represents a benzene ring or a stricture represented by the following general formula (2) (hereinafter referred to as a "benzimidazolone (2)"), provided that at least one of rings $A^1$, $A^2$, $A^3$ and $A^4$ is benzimidazolone (2):

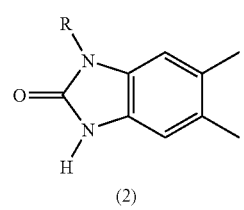

[Chemical Formula 5]

(2)

wherein R represents a hydrogen atom, an alkyl group having 1 to 4 carbon atoms, a phenyl group, tolyl group, or a xylyl group.

To synthesize the above compound (1), first, a dicyano benzimidazolone compound represented by the following general formula (3), which is a dinitrile compound having an imidazolone ring as the intermediate, is synthesized by the following synthesis method:

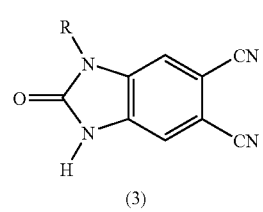

[Chemical Formula 6]

(3)

wherein R represents a hydrogen atom an alkyl group having 1 to 4 carbon atoms, a phenyl group, a tolyl group, or a xylyl group.

[Synthesis of Dicyano Benzimidazolone Compound]

The dicyano benzimidazolone compound represented by the general formula (3) (hereinafter referred to as a "compound (3)") can be obtained by reacting a compound represented by the following general formula (4) (hereinafter referred to as a "compound (4)") with urea or 1,1-carbonyl-diimidazole in an organic solvent such as acetonitrile at 50 to 130° C. for about 1 to 6 hours:

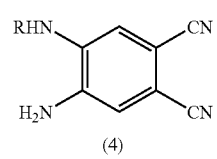

[Chemical Formula 7]

(4)

wherein R represents a hydrogen atom, an alkyl group having 1 to 4 carbon atoms, a phenyl group, a tolyl group, or a xylyl group.

The method for synthesizing a compound (4) in which R in the general formula (4) is a hydrogen atom includes, for example, a method comprising protecting an amino group of o-phenylenediamine with a tosyl group, brominating moieties at the 4- and 5-positions, performing deprotection, and reacting with copper cyanide thereby substituting a bromo group with a cyano group. This synthesis method is described in detail in Journal of the Chemical Society, 1170 (1962), and Chemistry-A European Journal, 9 (5), 1233 (2003). A compound (3) in which R in the general formula (3) is a hydrogen atom can be obtained by synthesizing the above compound (3) using this compound (4) in which R in the general formula (4) is a hydrogen atom.

Also, the method for synthesizing a compound (4) in which R is other than a hydrogen atom in the general formula (4) includes, for example, a method comprising nitrating moieties at the 4- and 5-positions of o-dibromobenzene, reacting with ammonia thereby reducing one of nitro groups to an amino group, monoalkylating or monoarylating the amino group, substituting a bromo group with a cyano group, and reducing a nitro group with tin chloride. This synthesis method is described in detail in Chemical Communication, 2236 (2002). A compound (3) in which R in the general formula (3) is other than a hydrogen atom can be obtained by synthesizing the above compound (3) using this compound (4) in which R in the general formula (4) is other than a hydrogen atom The compound (1) can be obtained by the following synthesis method (1) using the compound (3) obtained by the above synthesis method when all substituents of ring $A^1$, $A^2$, $A^3$ and $A^4$ in the general formula (1) are benzimidazolones (2), or can be obtained by the following synthesis method (2) when one to three rings among rings $A^1$, $A^2$, $A^3$ and $A^4$ are benzimidazolones (2) and the remainder are benzene rings.

Synthesis Method (1)

The compound (1) in which all of rings $A^1$, $A^2$, $A^3$ and $A^4$ in the general formula (1) are benzimidazolones (2) can be obtained by thermocondensing the compound (3) described above with a metal salt corresponding to a divalent to tetravalent metal atom represented by M in the general formula (1) in an organic solvent at 130 to 250° C. The phthalocyanine compound obtained by this synthesis is a phthalocyanine compound as a metal complex represented by the following general formula (5) hereinafter referred to as a "compound (5)"). By using two or more kinds of compounds (3), each having different R in the general formula (3), it is possible to obtain a phthalocyanine compound in which $R^1$, $R^2$, $R^3$ and $R^4$ in the following general formula (5) are different. In this synthesis method (1), by synthesizing without using a metal salt corresponding to the divalent to tetravalent metal atom, it is possible to obtain a metal-free phthalocyanine compound in which M in the following general formula (5) represents two hydrogen atoms:

[Chemical Formula 8]

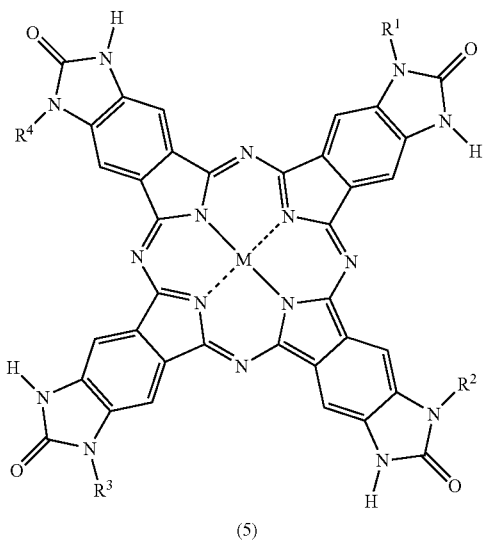

(5)

wherein M represents a divalent to tetravalent metal atom or two hydrogen atoms, and $R^1$ to $R^4$ each independently represents a hydrogen atom, an alkyl group having 1 to 4 carbon atoms, a phenyl group, a tolyl group, or a xylyl group.

The divalent to tetravalent metal atom represented by M in the general formula (1) includes, for example, atoms of magnesium, aluminum, titanium, vanadium, iron, cobalt, nickel, copper, zinc, platinum, and palladium. Among these metal atoms, a copper or zinc atom is preferable and a zinc atom is more preferable. The divalent to tetravalent metal atom represented by M in the general formula (1) corresponds to a divalent to tetravalent metal atom represented by M in the general formula (5).

As the metal salt corresponding to the divalent to tetravalent metal atom, for example, various salts such as halides, acetates, sulfates, nitrates, and carbonates can be used, and halides and acetates are preferable.

The organic solvent used to synthesize the compound (5) includes, for example, alcohols, glycols, trichlorobenzene, quinoline, α-chloronaphthalene, nitrobenzene, sulfolane, and N,N-dimethylformamide. The reaction may be conducted without using a solvent.

In the case of synthesizing the compound (5), an alkali or an organic amine such as diazabicycloundecene (hereinafter referred to as "DBU") or cyclohexylamine is preferably used as a catalyst because the yield is improved.

Synthesis Method (2)

A compound (1) in which one to three rings among ring $A^1$, $A^2$, $A^3$ and $A^4$ are benzimidazolones (2) and the others are benzene rings in the general formula (1) can be obtained by thermocondensing the compound (3) obtained above, phthalonitrile, and a metal salt corresponding to a divalent to tetravalent metal atom represented by M in the general formula (1) in an organic solvent at about 130 to 250° C. The phthalocyanine compound obtained by this synthesis is a phthalocyanine compound as a metal complex represented by the following general formula (6)(herein referred to as a "compound (6)"). By using two or more kinds of compounds (3), each having different R in the general formula (3), it is possible to obtain a phthalocyanine compound in which each benzimidazolone (2) in rings $B^1$, $B^2$ and $B^3$ in the following general formula (6) is different. In the synthesis method (2), by synthesizing without using a metal salt corresponding to the divalent to tetravalent metal atom, it is possible to obtain a metal-free phthalocyanine compound in which M in the following general formula (6) represents two hydrogen atoms:

[Chemical Formula 9]

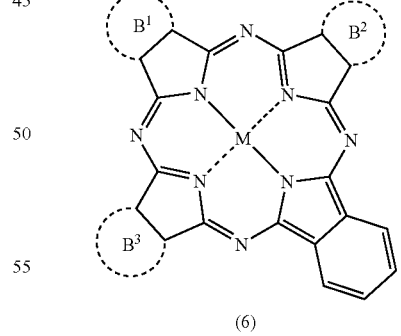

(6)

wherein M represents a divalent to tetravalent metal atom or two hydrogen atoms, and rings $B^1$, $B^2$ and $B^3$ each independently represents a benzene ring or benzimidazolone (2), provided that at least one of rings $B^1$, $B^2$ and $B^3$ is benzimidazolone (2).

The metal salt corresponding to the divalent to tetravalent metal atom used in this synthesis method (2), the divalent to tetravalent metal atom, the organic solvent and the catalyst may be the same as those used in the synthesis method (1).

In the above synthesis method (2), when a ratio of the compound (3) and phthalonitrile to be charged as raw materials is varied, hue of the finally obtained compound (6) varies. By increasing a charging ratio of phthalonitrile, the result compound (6) shows more bluish hue and high chroma. Therefore, the charging ratio of phthalonitrile can be appropriately selected so as to obtain desired hue and chroma, but is preferably within a range from 15 to 75 mass % based on the total amount of the compound (3) and phthalonitrile.

A compound (1) in which imidazolone is introduced into phthalocyanine can be obtained by the above synthesis method (1) or (2). In this compound (1), since imidazolone has a carbonyl group, unlike a compound (a) as the above-described phthalocyanine compound having an imidazole ring, it becomes possible to form an intermolecular hydrogen bond between this carbonyl group and a hydrogen atom bonded with a nitrogen atom in imidazolone of the other molecule, resulting in excellent resistance to an organic solvent and an acid.

When all of rings $A^1$, $A^2$, $A^3$ and $A^4$ are benzimidazolones (2) in the general formula (1), hue of the compound (1) becomes green. On the other hand, when one to three rings among rings $A^1$, $A^2$, $A^3$ and $A^4$ are benzimidazolones (2) and the remaindered are benzene rings, hue becomes bluish green. As the number of benzene ring increases in rings $A^1$, $A^2$, $A^3$ and $A^4$, hue becomes more bluish green. Rings $A^1$, $A^2$, $A^3$ and $A^4$ are preferably composed of benzimidazolone (2) and a benzene ring because chroma is enhanced. Furthermore, in benzimidazolone (2), R in the general formula (2) is preferably a hydrogen atom, because the number of moieties, which form the above intermolecular hydrogen bond, increases and therefore resistance to an organic solvent and an acid is more enhanced.

As described above, since hue of the phthalocyanine compound of the present invention can be varied according to the kind of rings $A^1$, $A^2$, $A^3$ and $A^4$ in the general formula (1), desired hue can be obtained by appropriately selecting rings $A^1$, $A^2$, $A^3$ and $A^4$ from among benzimidazolone (2) and benzene rings.

In the compound (1), phthalocyanine compounds represented by the following formulas (7-a) to (7-e) are more preferable.

[Chemical Formula 10]

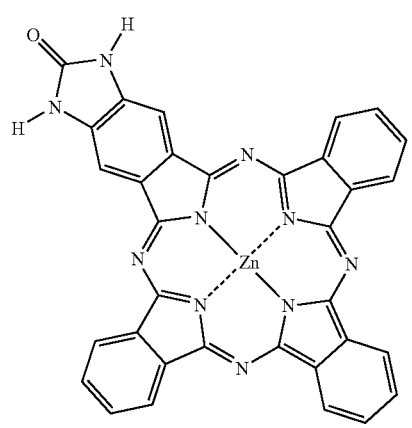

(7-a)

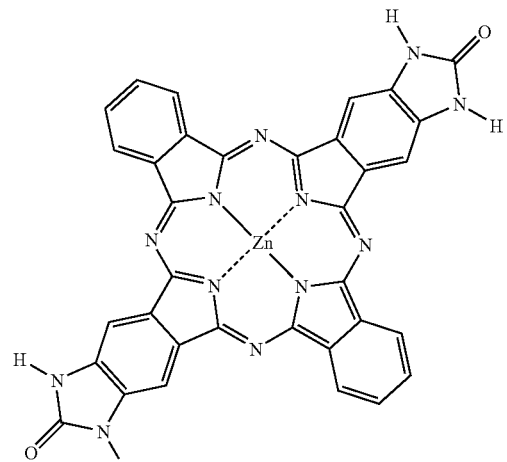

(7-b)

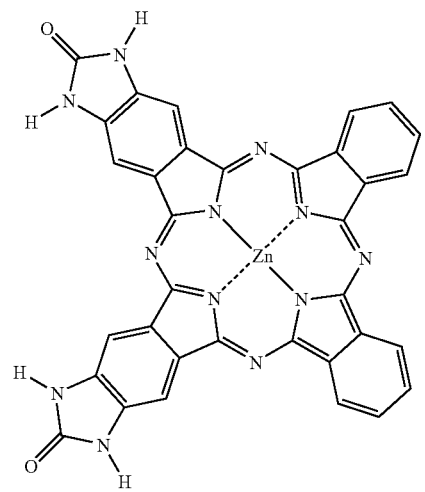

(7-c)

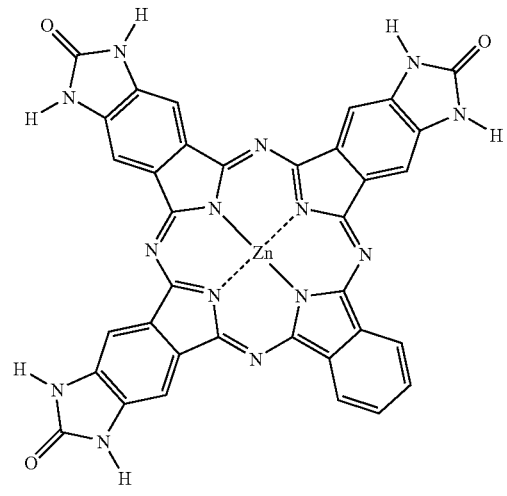

(7-d)

-continued

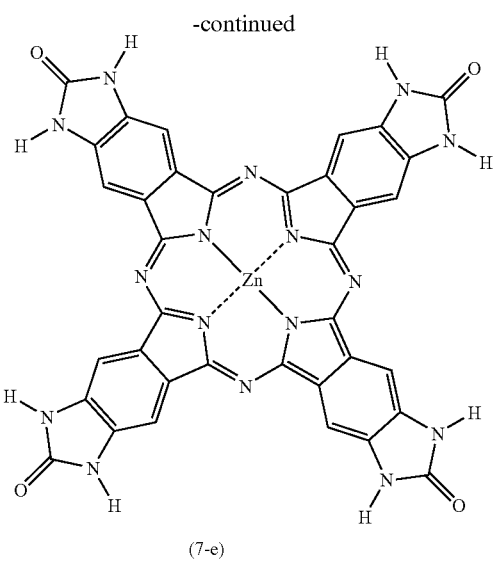

(7-e)

By the above synthesis method, the compound (1) is obtained as a green crude pigment. When the compound is used as a coloring agent, a pigmentation treatment is preferably conducted. This pigmentation treatment includes, for example, a milling treatment such as solvent salt milling, salt milling, dry milling, solvent milling, or acid pasting, or a solvent heating treatment. The particle size of the pigment can be simultaneously adjusted by these pigmentation treatments.

When the phthalocyanine compound of the present invention is used as a green pigment, the phthalocyanine compound is preferably subjected to the above pigmentation treatment thereby adjusting the particle size of the pigment within a range from 0.01 to 1 µm.

The coloring composition of the present invention is a composition containing the phthalocyanine compound of the present invention as a coloring agent and applications thereof include printing inks, coating materials, colored plastics, toners, ink jet inks, color pastes for color filter, and color resists.

EXAMPLES

The present invention will now be described in detail by way of Examples.

Synthesis Example 1

In 100 parts by mass of dehydrated acetonitrile 15 parts by mass of 1,2-diamino-4,5-dicyanobenzene and 19.5 parts by mass of 1,1-carbonyldiimidazole were added, followed by reaction while stirring at 70° C. for 3 hours. The resulting reaction product was cooled to room temperature and the precipitated solid was filtered, washed with water and then dried to obtain 16.9 parts by mass (yield: 96.5%) of a peachish white solid.

With respect to the peachish white solid obtained in Synthesis Example 1, $^1$H-NMR analysis (using a nuclear magnetic resonance spectrometer "JNM-LA300" manufactured by JEOL Ltd.) in a dimethyl sulfoxide (hereinafter referred to as "DMSO")-$d_6$ solution and infrared spectrophotometry (using a Fourier transform infrared spectrophotometer "FT/IR-550" manufactured by JASCO Corporation) were conducted to obtain the following analytical results. A spectrum obtained by infrared spectrophotometry is shown in FIG. 1.

<$^1$H-NMR Analysis>
$^1$H-NMR (DMSO-$d_6$): δ=7.61 (s), 11.67 (s, br)

<Infared Spectrophotomtry>
3316 cm$^{-1}$: N—H stretching vibration of imidazolone
2240 cm$^{-1}$: C≡N stretching vibration of cyano group
1709, 1726 cm$^{-1}$: C=O stretching vibration of imidazolone It was confirmed by the above results that the peachish white solid obtained in Synthesis Example 1 is a dicyano benzimidazolone compound represented by the following formula (8).

[Chemical Formula 11]

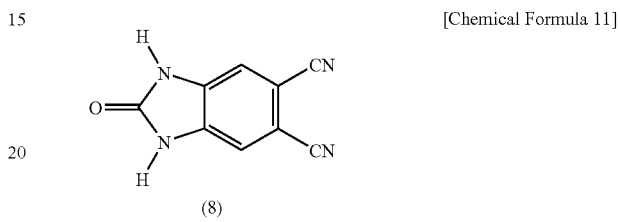

(8)

Synthesis Example 2

Synthesis of Phthalocyanine Compound in which M is a Copper Atom and all of $R^1$ to $R^4$ are Hydrogen Atoms in the General Formula (5)

In 32 parts by mass of trichlorobenzene, 10 parts by mass of 5,6-dicyano benzimidazolone obtained in Synthesis Example 1, 1.4 parts by mass of copper (I) chloride and 10 parts by mass and DBU were added, followed by reaction while stirring at 180° C. for 6 hours. The resulting reaction product was cooled to room temperature and the precipitated solid was filtered. The resulting solid was washed in turn with acetone, methanol, 10 mass % hydrochloric acid, 8 mass % ammonia in water and water, and then dried to obtain 7.3 parts by mass (yield: 67.2%) of a green solid.

Figure 2:
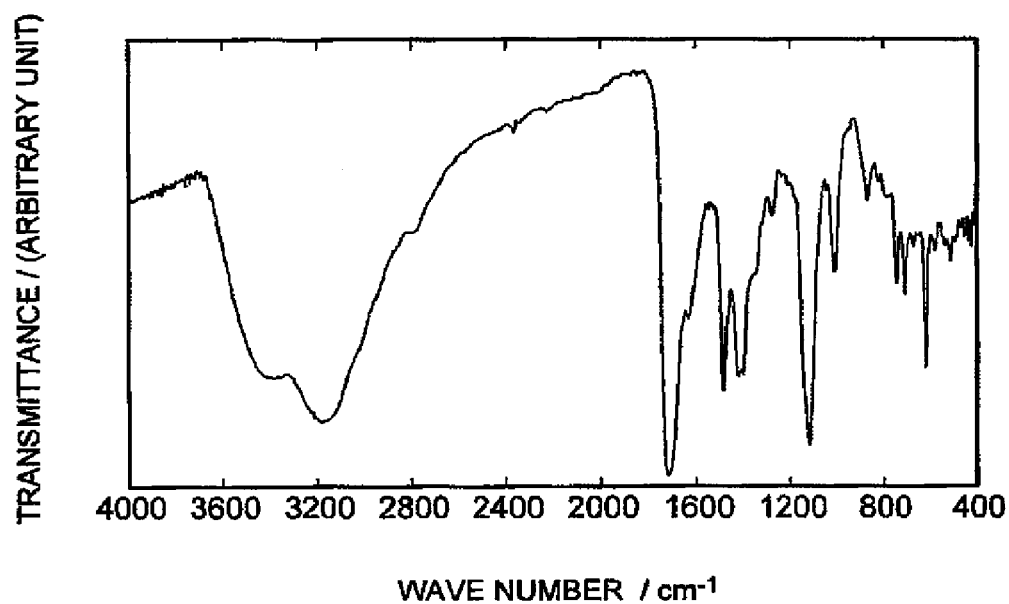
FIG. 2 is a graph showing an infrared spectrum of copper tetrabenzimidazolonoporphyrazine synthesized in Synthesis Example 2.
Figure 3:
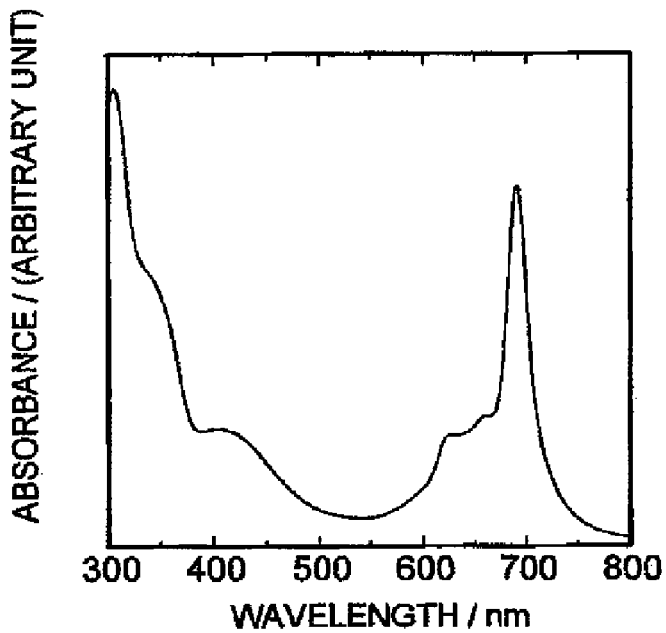
FIG. 3 is a graph showing an optical absorption spectrum in DMSO solution of copper tetrabenzimidazolonoporphyrazine synthesized in Synthesis Example 2.

With respect to the green solid obtained above, FAB/MS Analysis (mass spectrometer manufactured by JEOL Ltd. "JMS-LX2000"), infrared spectrophotometry (using a Fourier transform infrared spectrophotometer "FT/IR-550" manufactured by JASCO Corporation) and measurement of an optical absorption spectrum in a DMSO solution (using an automatic recording spectrophotometer "U-3500" manufactured by Hitachi, Ltd.) were conducted to obtain the following analytical results. A spec obtained by infrared spectrophotometry is shown in FIG. 2 and an optical absorption spectrum is shown in FIG. 3.

<FAB/MS Analysis>
m/z=800 (M+H)$^+$

<Infrared Spectrophotometry>
3178 cm$^{-1}$: N—H stretching vibration of imidazolone
1716 cm$^{-1}$: C=O stretching vibration of imidazolone <Optical Absorption Spectrum>
Absorption wavelength: 306, 404, 626, 691 nm (in DMSO)

It was confirmed by the above results that the green solid obtained in Synthesis Example 2 is copper tetrabenzimidazolonoporphyrazine represented by the following formula (9).

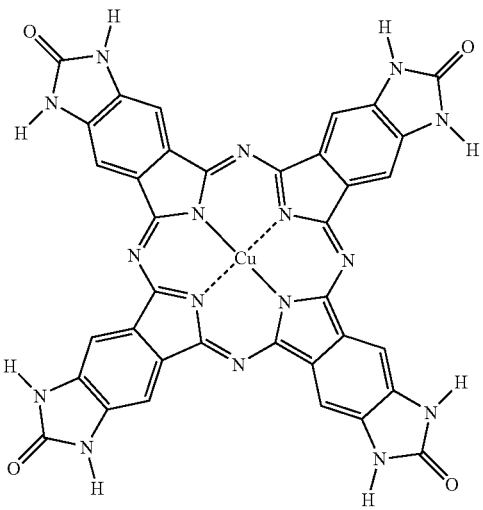

(9)

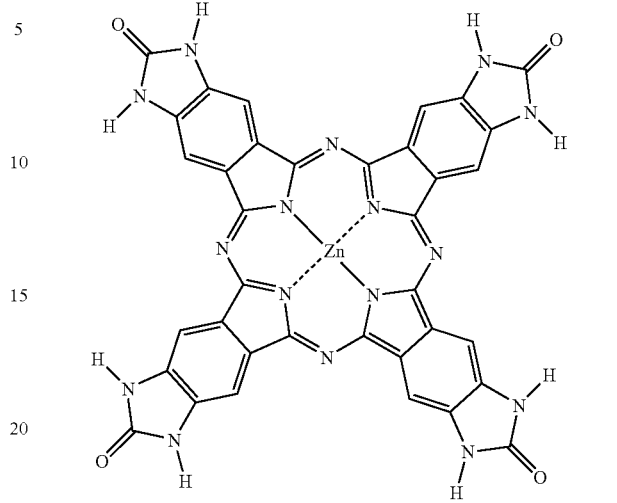

(10)

Synthesis Example 3

Synthesis of Phthalocyanine Compound in which M is a Zinc Atom and all of $R^1$ to $R^4$ are Hydrogen Atoms in the General Formula (5)

In 175 parts by mass of 1-pentanol, 15 parts by mass of 5,6-dicyano benzimidazolone obtained in Synthesis Example 1, 5.0 parts by mass of urea, 3.5 parts by mass of zinc acetate and 12.5 parts by mass of DBU were added, followed by reaction while siring at 140° C. for 6 hours. The resulting reaction product was cooled to room temperature and the precipitated solid was filtered. The resulting solid was washed in turn with acetone, methanol, 3 mass % sulfuric acid, 8 mass % ammonia in water and water, and then dried to obtain 4.0 parts by mass (yield: 24.8%) of a green solid.

Figure 4:
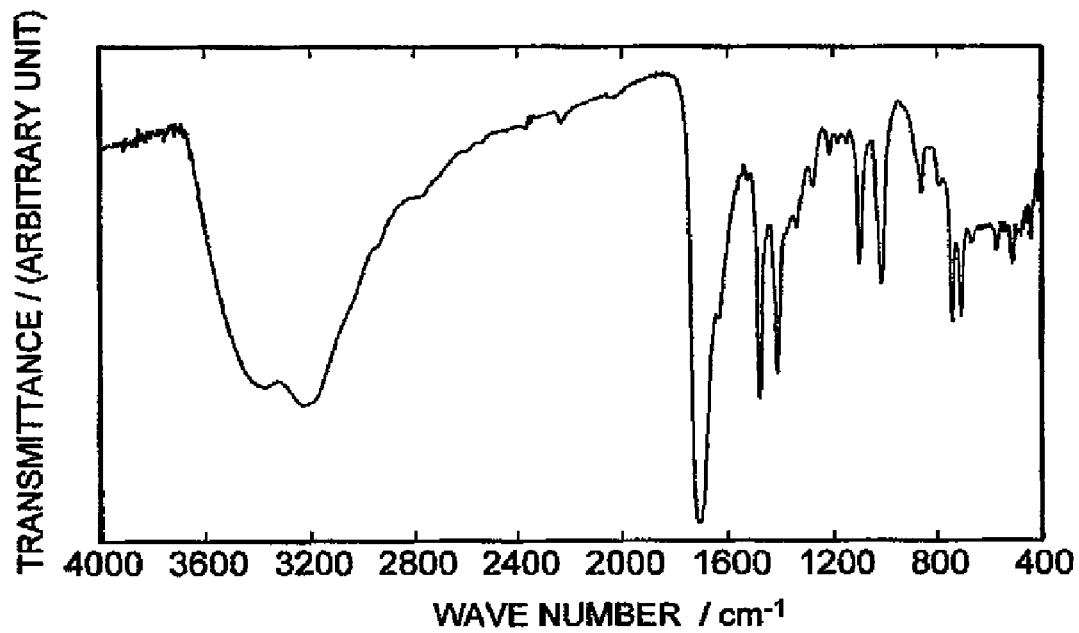
FIG. 4 is a graph showing an infrared spectrum of zinc tetrabenzimidazolonoporphyrazine synthesized in Synthesis Example 3.
Figure 5:
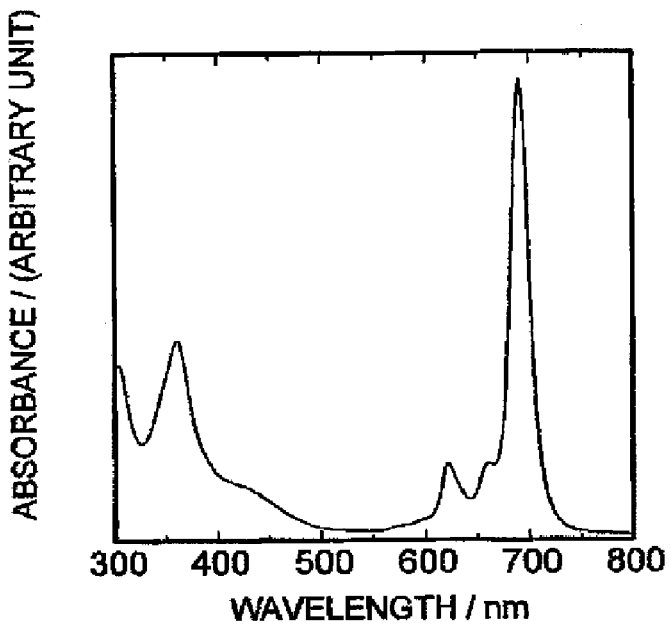
FIG. 5 is a graph showing an optical absorption spectrum in a DMSO solution of zinc tetrabenzimidazolonoporphyrazine synthesized in Synthesis Example 3.

With respect to the green solid obtained above, FAB/MS Analysis (using a mass spectrometer "JMS-LX2000" manufactured by JEOL Ltd.), infrared spectrophotometry (using a Fourier transform infrared spectrophotometer "FT/IR-550" manufactured by JASCO Corporation F) and measurement of an optical absorption spectrum in a DMSO solution (using an automatic recording spectrophotometer "U-3500" manufactured by Hitachi, Ltd.) were conduced to obtain the following analytical results. A spectrum obtained by infrared spectrophotometry is shown in FIG. 4 and an optical absorption spectrum is shown in FIG. 5.

<FAB/MS Analysis> m/z=801 (M+H)$^+$

<Infrared Spectrophotometry>

3228 cm$^{-1}$: N—H stretching vibration of imidazolone 1708 cm$^{-1}$: C=O synching vibration of imidazolone <Optical Absorption Spectrum>

Absorption wavelength: 303, 361, 622, 691 nm (in DMSO)

It was confirmed by the above results that the green solid obtained in Synthesis Example 3 is zinc tetrabenzimidazolonoporphyrazine represented by the following formula (10), Synthesis Example 4

Synthesis 1 of Compounds Represented by the Formulas (7-a) to (7-e)

In 10 parts by mass of 1-octanol, 1.6 parts by mass of 5,6-dicyano benzimidazolone obtained in Synthesis Example 1, 0.4 parts by mass of phthalonitrile, 0.7 parts by mass of urea, 0.5 parts by mass of zinc acetate and 0.7 parts by mass of DBU, followed by reaction while stirring at 170° C. for 6 hours. The resulting reaction product was cooled to room temperature and the precipitated solid was filtered. The resulting solid was washed in turn with acetone, methanol, 10 mass % hydrochoric acid, water and methanol, and then dried to obtain 1.3 parts by mass of a slightly bluish green solid.

Figure 6:
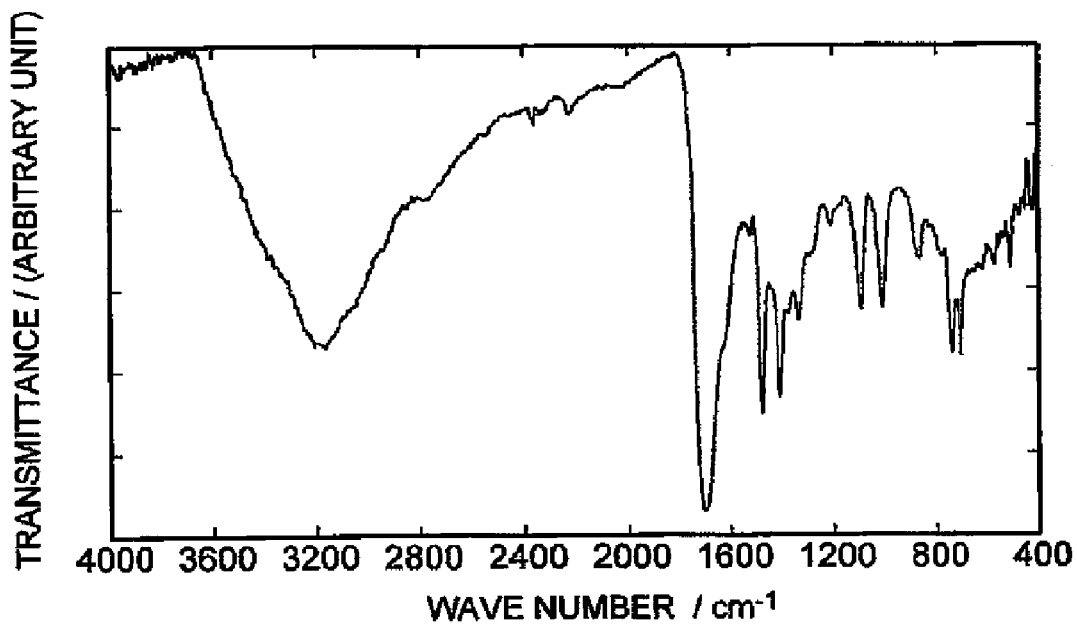
FIG. 6 is a graph showing an infrared spectrum of a mixture (1) of zinc benzimidazolonoporphyrazine compounds synthesized in Synthesis Example 4.
Figure 7:
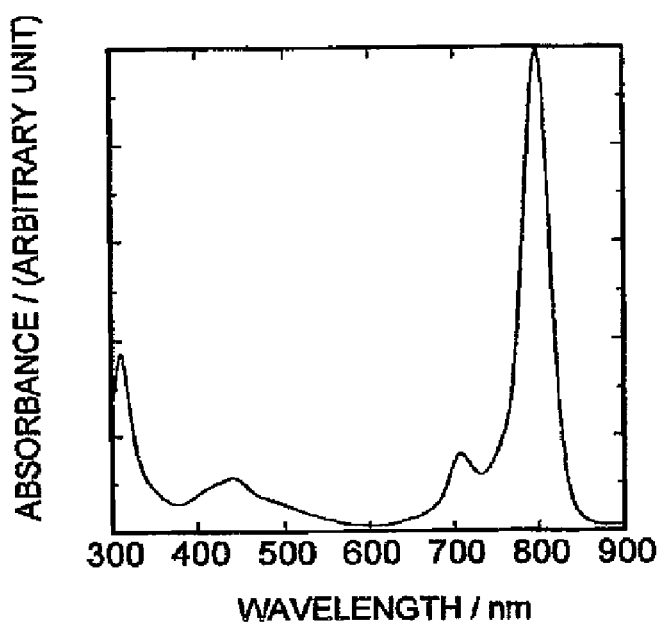
FIG. 7 is a graph showing an optical absorption spectrum in a concentrated sulfuric acid solution of a mixture (1) of zinc benzimidazolonoporphyrazine compounds synthesized in Synthesis Example 4.

With respect to the slightly blush green solid obtained above, FD/MS Analysis (using a mass spectrometer "JMS-700" manufactured by JEOL Ltd.), infrared spectrophotometry (using a Fourier transform infrared spectrophotometer "FT/IR-550" manufactured by JASCO Corporation) and measurement of an optical absorption spectrum in a concentrated sulfuric acid (using an automatic recording spectrophotometer "U-3500" manufactured by Hitachi, Ltd.) were conducted to obtain the following analytical results. A spectrum obtained by infrared spectrophotometry is shown in FIG. 6 and an optical absorption spectrum is shown in FIG. 7.

<FD/MS Analysis> m/z=576, 632, 688, 744, 800

<Infrared Spectrophotometry>

3168 cm$^{-1}$: N—H stretching vibration of imidazolone 1704 cm$^{-1}$: C=O stretching vibration of imidazolone <Optical Absorption Spectrum>

Absorption wavelength: 311, 441, 707, 798 nm (in concentrated sulfuric acid)

It was confirmed by the above results that the slightly bluish green solid obtained in Synthesis Example 4 is a mixture of zinc phthalocyanine and five zinc benzimidazolonoporphyrazine compounds represented by the following formulas (7-a) to (7-e) (hereinafter referred to as a "mixture (1) of zinc benzimidazolonoporphyrazines").

[Chemical Formula 14]

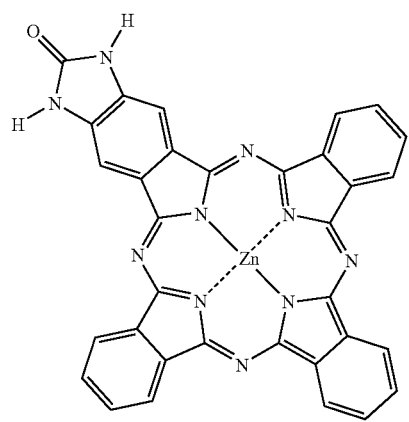

(7-a)

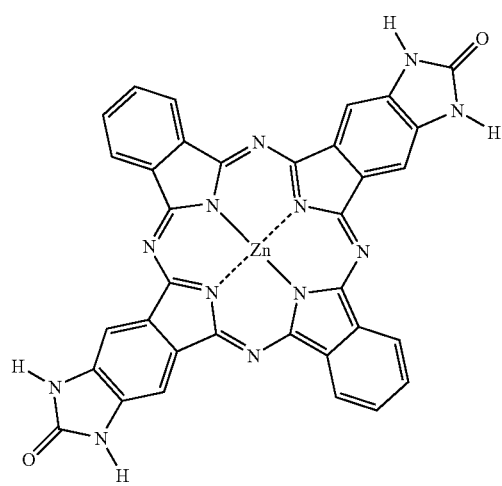

(7-b)

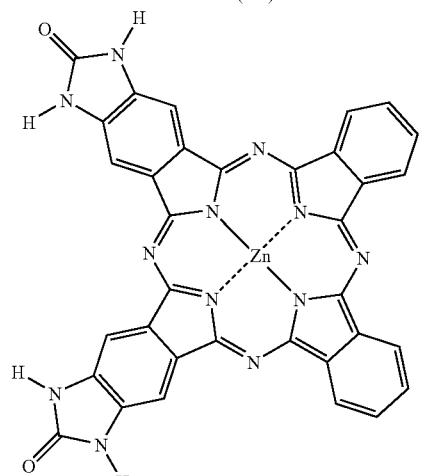

(7-c)

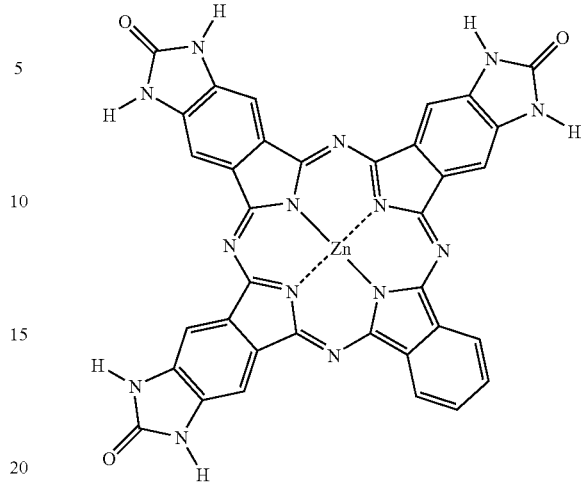

(7-d)

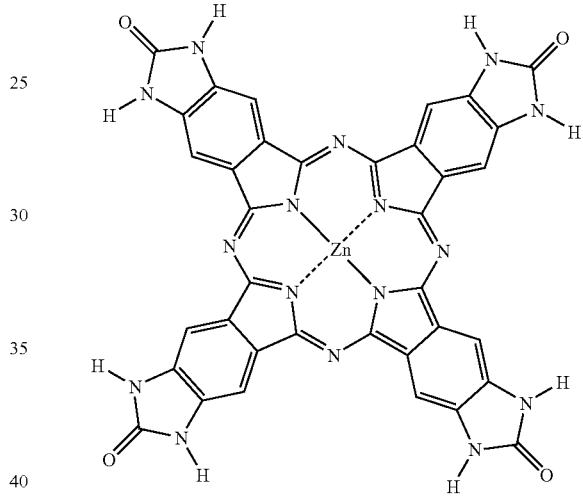

(7-e)

Synthesis Example 5

Synthesis 2 of the Formulas (7-a) to (7-e)

In 10 parts by mass of 1-octanol, 1.2 parts by mass of 5,6-dicyano benzimidazolone obtained in Synthesis Example 1, 0.8 parts by mass of phthalonitrile, 0.7 parts by mass of urea, 0.6 parts by mass of zinc acetate and 0.7 parts by mass of DBU were added, followed by reaction while stirring at 170° C. for 6 hours. The resulting reaction product was cooled to room temperature and the precipitated solid was filtered. The resulting solid was washed in turn with acetone, methanol, 10 mass % hydrochloric acid, water, methanol, and then dried to obtain 1.4 parts by mass of a slightly bluish green solid.

Figure 8:
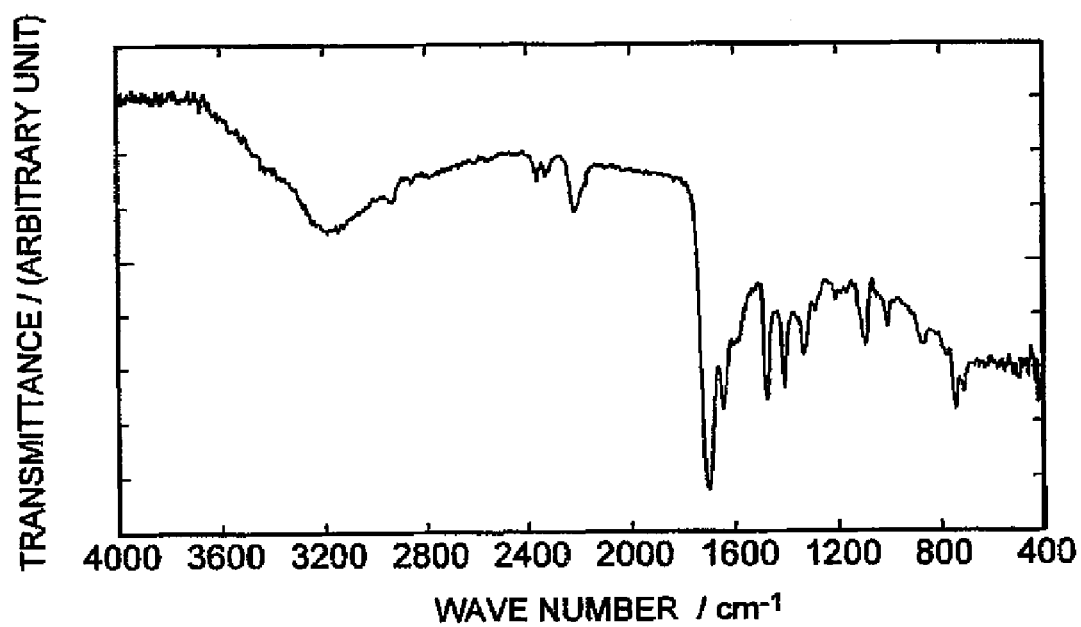
FIG. 8 is a graph showing an infrared spectrum of a mixture (2) of zinc benzimidazolonoporphyrazine compounds synthesized in Synthesis Example 5.
Figure 9:
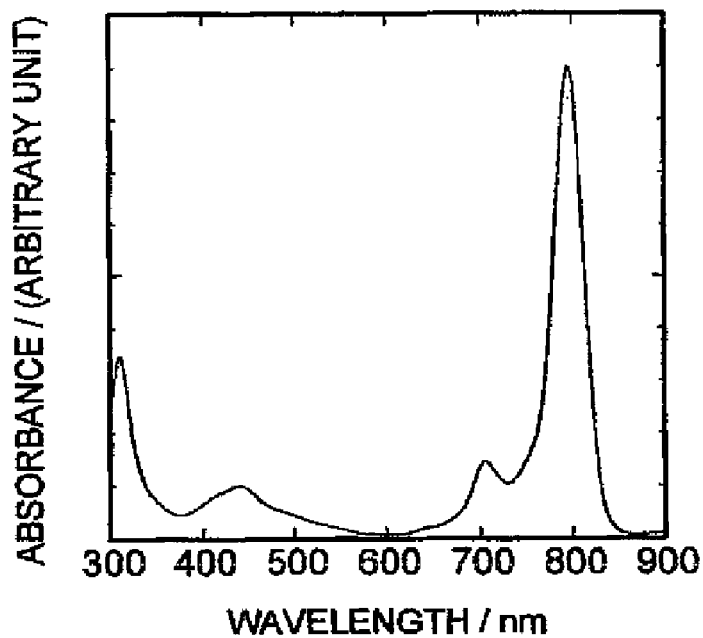
FIG. 9 is a graph showing an optical absorption spectrum in a concentrated sulfuric acid solution of a mixture (2) of zinc benzimidazolonoporphyrazine compounds synthesized in Synthesis Example 5.

With respect to the bluish green solid obtained above, FD/MS Analysis (using a mass spectrometer "JMS-700" manufactured by JEOL Ltd.), infrared spectrophotometry (using a Fourier transform infrared spectrophotometer "FT/IR-550" manufactured by JASCO Corporation) and measurement of an optical absorption spectrum in a concentrated sulfuric acid solution (using an automatic recoding spectrophotometer "U-3500" manufactured by Hitachi, Ltd.) were conducted to obtain the following analytical results. A spectrum obtained by infrared spectrophotometry is shown in FIG. 8 and an optical absorption spectrum is shown in FIG. 9.

<FAB/MS Analysis> m/z=576, 632, 688, 744, 800

<Infrared Spectrophotometry>

3182 cm$^{-1}$: N—H stretching vibration of imidazolone
1702 cm$^{-1}$: C=O stretching vibration of imidazolone <Optical Absorption Spectrum>

Absorption wavelength: 310, 440, 705, 796 nm (in concentrated sulfuric acid solution)

It was confirmed by the above results that the bluish green solid obtained in Synthesis Example 5 is a mixture of zinc phthalocyanine and five zinc benzimidazolonoporphyrazine compounds represented by the above formulas (7-a) to (7-e) hereinafter referred to as a mixture (2) of "zinc benzimidazolonoporphyrazine compounds).

Example 1

2.2 parts by mass of zinc tetrabenzimidazolonoporphyrazine obtained in Synthesis Example 3 was added to 40 parts by mass of N, N-dimethylformamide and a solvent heating treatment was conducted at 150° C. for 6 hours. After the heat treatment the green powder was filtered and then dried to obtain a green pigment having an average particle size of 0.5 μm.

Using the resulting green pigment of zinc tetrabenzimidazolonoporphyrazine, the following baking coating material coatability test and chemical resistance test were conducted.

<Baked Coating Material Coatability Test>

4 parts by mass of a green pigment, 10 parts by mass of a mixed resin of 70% of an alkyd resin for baking coating material ("Bekkozol J-524-IM60" manufactured by Dainippon Ink and Chemicals, Incorporated.) and 30% of a melamine resin ("Super Bekkamine G-821-60" manufactured by Dainippon Ink and Chemicals, Incorporated.), 7 parts by mass of xylene and 3 parts by mass of n-butanol were dispersed with a paint conditioner for 2 hours using glass beads as a grinding media. Then, 50 parts by mass of an acrylmelamine resin was added, followed by mixing with the paint conditioner for 5 minutes. The resulting green coating material composition was applied on a polyester film using an applicator and then baked at 130° C. for 30 minutes. The resulting coating film showed a glossy green color.

Figure 10:
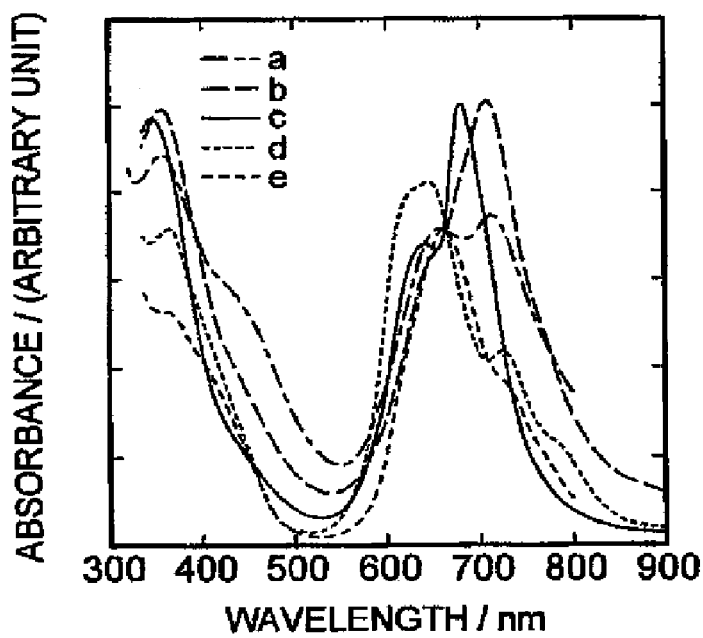
FIG. 10 is a graph showing an optical absorption sped of a baked coating film obtained in a baking coating material coatability test. (a: Example 1; b: Example 2; c: Example 3; d. Comparative Example 1; e: Comparative Example 2)

With respect to the coating film obtained above, an optical absorption spectrum was measured using a spectrophotometer (using an automatic recording spectrophotometer "3-3500" manufactured by Hitachi, Ltd.). Absorption wavelengths of this coating film were 357, 657, and 713 nm. The optical absorption spectrum obtained by the measurement is shown in FIG. 10.

<Chemical Resistance Test>

1 Part by mass of a green pigment and 20 parts by mass of an organic solvent or an acid described in the following Table 1 were charged in a lidded container, sealed, shaken for 30 seconds and then allowed to stand for 15 minutes. The lidded container was shaken again for 30 seconds and allowed to stand for 30 minutes, followed by filtration. Coloration of the filtrate was visually observed and evaluation was conducted according to the following criteria.

Good: No coloration of a filtrate was visually confirmed.

Poor: Coloration of a filtrate was visually confirmed.

Example 2

In the same manner as in Example 1, except a mixture (1) of zinc benzimidazolonoporphyrazine compounds obtained in Synthesis Example 4 was used as a green pigment in place of zinc tetrabenzimidazolonoporphyrazine obtained in Synthesis Example 3, a baking coating material coatability test and a chemical resistance test were conducted.

Example 3

In the same manner as in Example 1, except that a mixture (2) of zinc benzimidazolonoporphyrazine compounds obtained in Synthesis Example 5 was used as a green pigment in place of zinc tetrabenzimidazolonoporphyrazine obtained in Synthesis Example 3, a baking coating material coatability test and a chemical resistance test were conducted.

Comparative Example 1

In the same manner as in Example 1, except that a chlorinated copper phthalocyanine pigment ("Fastogen Green S", C.I. Pigment Green 7 manufactured by Dainippon Ink and Chemicals, Incorporated) was used as a green pigment in place of zinc tetrabenzimidazolonoporphyrazine obtained in Synthesis Example 3, a baling coating material coatability test and a chemical resistance test were conducted.

Comparative Example 2

In the same manner as in Example 1, except that a brominated copper phthalocyanine pigment ("Fastogen Green 2YK-CF", C.I. Pigment Green 36 manufactured by Dainippon Ink and Chemicals, Incorporated.) was used as a green pigment in place of zinc tetrabenzimidazolonoporphyrazine obtained in Synthesis Example 3, a baking coating material coatability test and a chemical resistance test were conducted.

Test results of the green pigments of Examples 1 to 3 and Comparative Examples 1 and 2 are shown in Table 1. With regard to the item of halogen-free in Table 1, a halogen-free pigment was described "Yes", while a no halogen-fee pigment was described as "No".

TABLE 1

| Compound | Example 1 Zinc tetrabeazimidazolono- porphyrazine | Example 2 Mixture (1) of zinc benzimidazolono- porphyrazines | Example 3 Mixture (2) of zinc benzimidazolono- porphyrazines | Comparative Example 1 Chlorinated copper phthalocyanine | Comparative Example 2 Brominated copper phthalocyanine |
|---|---|---|---|---|---|
| Halogen-free | Yes | Yes | Yes | No | No |
| Hue | Green | Slighty bluish green | Bluish green | Bluish green | Green |
| Absorption wavelength of baked coating film (nm) | 357 657 713 | 355 707 | 346 642 680 | 363 646 | 366 662 |

TABLE 1-continued

| Compound | Example 1 Zinc tetrabeazimidazolono-porphyrazine | Example 2 Mixture (1) of zinc benzimidazolono-porphyrazines | Example 3 Mixture (2) of zinc benzimidazolono-porphyrazines | Comparative Example 1 Chlorinated copper phthalocyanine | Comparative Example 2 Brominated copper phthalocyanine |
|---|---|---|---|---|---|
| Chemical resistance test | | | | | |
| Methanol | Good | Good | Good | Good | Good |
| Acetone | Good | Good | Good | Good | Good |
| Ethyl acetate | Good | Good | Good | Good | Good |
| Xylene | Good | Good | Good | Good | Good |
| 2 mass % HCl | Good | Good | Good | Good | Good |

As is apparent from the results shown in Table 1, the phthalocyanine compound of the present invention can be used as a halogen-free green pigment and has resistance to an organic solvent and an acid, which is equivalent to that of a chlorinated copper phthalocyanine pigment or a brominated copper phthalocyanine pigment known as an existing green pigment having high chemical resistance.

INDUSTRIAL APPLICABILITY

The phthalocyanine compound of the present invention has green hue and also has resistance to an organic solvent and an acid, and is therefore useful as a green pigment. Also, the phthalocyanine compound of the present invention is halogen-free and therefore has features such as high safety and low environmental burden. Thus, the phthalocyanine compound of the present invention is used very usefully in place of a halogenated phthalocyanine-based pigment as an existing green pigment in applications which require environmental measures.

The phthalocyanine compound of the present invention can be used as a coloring agent in wide applications such as printing inks, coating materials, colored plastics, toners, ink jet ins, and color filters because of having the features described above.

The invention claimed is:

1. A compound represented by the following general formula (1):

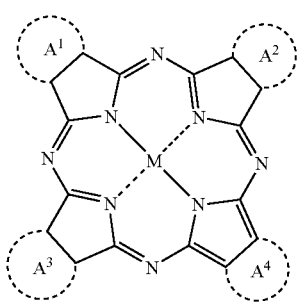

(1)

wherein M represents a divalent to tetravalent metal atom or two hydrogen atoms, and rings $A^1$, $A^2$, $A^3$ and $A^4$ each independently represents a benzene ring or a structure represented by the following general formula (2), provided that at least one of rings $A^1$, $A^2$, $A^3$ and $A^4$ is a structure represented by the following general formula (2):

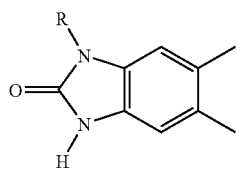

(2)

wherein R represents a hydrogen atom, an alkyl group having 1 to 4 carbon atoms, a phenyl group, a tolyl group, or a xylyl group.

2. The compound according to claim 1, wherein the divalent to tetravalent metal atom represented by M is a copper or zinc atom in the general formula (1).

3. The compound according to claim 1, wherein R is a hydrogen atom in the general formula (2).

4. The compound according to claim 1, wherein all of the rings $A^1$, $A^2$, $A^3$ and $A^4$ in the general formula (1) are structures represented by the general formula (2).

5. A method for preparing the compound according to claim 1, which comprises a step of thermocondensing a dicyano benzimidazolone compound represented by the following general formula (3), phthalonitrile, and a metal salt corresponding to a divalent to tetravalent metal atom represented by M in the general formula (1),

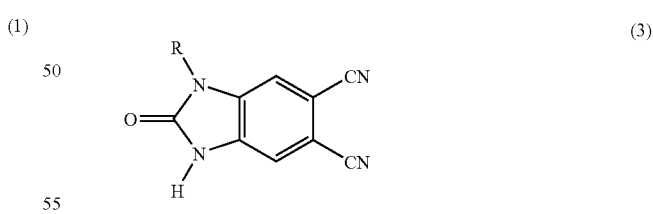

(3)

wherein R represents a hydrogen atom, an alkyl group having 1 to 4 carbon atoms, a phenyl group, a tolyl group, or a xylyl group.

6. A method for preparing the compound according to claim 4, which comprises a step of thermocondensing a dicyano benzimidazolone compound represented by the following general formula (3), and a metal salt corresponding to a divalent to tetravalent metal atom represented by M in the general formula (1),

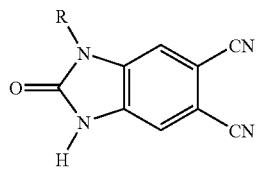

(3)

wherein R represents a hydrogen atom, an alkyl group having 1 to 4 carbon atoms, a phenyl group, a tolyl group, or a xylyl group.

7. The method for preparing the compound according to claim 5, wherein the metal salt is a salt selected from the group consisting of halides, acetates, sulfates, nitrates, and carbonates.

8. The method for preparing the compound according to claim 5, wherein the divalent to tetravalent metal atom represented by M in the general formula (1) is a metal atom selected from the group consisting of magnesium, aluminum, titanium, vanadium, iron, cobalt, nickel, copper, zinc, platinum, and palladium.

9. The method for preparing the compound according to claim 6, wherein the metal salt is a salt selected from the group consisting of halides, acetates, sulfates, nitrates, and carbonates.

10. The method for preparing the compound according to claim 6, wherein the divalent to tetravalent metal atom represented by M in the general formula (1) is a metal atom selected from the group consisting of magnesium, aluminum, titanium, vanadium, iron, cobalt, nickel, copper, zinc, platinum, and palladium.

11. A composition containing the compound according to claim 1, as a coloring agent, and resin.

* * * * *